United States Patent [19]

Vida et al.

[11] 4,217,274

[45] Aug. 12, 1980

[54] METHOXYETHOXYMETHYL ESTERS OF PENICILLINS

[75] Inventors: Julius A. Vida, Greenwich, Conn.; Kenneth A. Kerridge, Syracuse, N.Y.

[73] Assignee: Bristol-Myers Company, New York, N.Y.

[21] Appl. No.: 974,451

[22] Filed: Dec. 29, 1978

[51] Int. Cl.$^2$ ............................................ C07D 499/32
[52] U.S. Cl. .................................. 260/239.1; 424/271; 260/245.2 R; 424/246; 544/30
[58] Field of Search ................ 260/239.1 R, 306.7 C, 260/239.1 A, 239.1 AM, 245.2, 239.1 TB

[56] References Cited

U.S. PATENT DOCUMENTS 3,996,236  12/1976  Sleezer et al. ................. 260/306.7 C

FOREIGN PATENT DOCUMENTS 1488308  10/1977  United Kingdom .

OTHER PUBLICATIONS

Corey et al., Tetrahedron Letters, No. 11, pp. 809–812, 1976.

*Primary Examiner*—Nicholas S. Rizzo
*Attorney, Agent, or Firm*—Herbert W. Taylor, Jr.

[57] ABSTRACT

β-Methoxyethoxymethyl esters of cephalosporins and penicillins are exemplified by such esters of hetacillin and heta-amoxicillin were synthesized and found to exhibit advantageous biological properties.

4 Claims, No Drawings

METHOXYETHOXYMETHYL ESTERS OF PENICILLINS

BACKGROUND OF THE INVENTION

1. Field of the Invention

This invention provides new chemical compounds which are particular esters of the group of acids known as β-lactam antibiotics including especially the penicillins and cephalosporins.

2. Description of the Prior Art

Many β-lactam antibiotics have been converted to esters.

For examples in the area of penicillins of the ampicillin and amoxicillin type see U.S. Pat. No. 3,996,236, U.K. Pat. No. 1,488,308 and Farmdoc 81300T.

Some previous publications on penicillin esters are reviewed briefly in U.S. Pat. No. 3,996,236 as follows:

Esters of benzylpenicillins are disclosed in British Pat. No. 1,003,479 and U.S. Pat. No. 2,650,218, acyloxymethyl esters of ampicillin are discussed by W. V. Daehne et al. in J. Med. Chem., 13(4), 607–612 (1970). This publication also refers to early publications on the hydrolysis of esters. The pivaloyloxymethyl ester of ampicillin is also disclosed in U.S. Pat. Nos. 3,660,575 and 3,697,507. Various penicillin esters are also disclosed, for example, in U.S. Pat. No. 3,528,965 and U.K. Pat. No. 1,267,936. Various esters of 6-aminopenicillanic acid have been disclosed, for example, in U.S. Pat. Nos. 3,652,546 and 3,399,207. The crystalline toluene-p-sulphonate of the methoxymethyl ester of 6-aminopenicillanic acid was described by Jackson et al., Chemical Communications, 1970, pages 14–15. Methoxymethyl benzylpenicillinate and other penicillin esters are described by Jansen et al., J. Chem. Soc., 2127–32 (1965) and that publication refers to earlier publications such as Johnson, J. Amer. Chem. Soc., 75, 3636 (1953) and Barnden et al., J. Chem. Soc., 3733 (1953). The Jansen et al. publication is referred to in U.K. Pat. No. 1,217,143 published Dec. 31, 1970 (but not in the corresponding U.S. Pat. No. 2,650,218) in its generic disclosure on page 2 which names various specific esters of penicills, including methoxymethyl, and suggests acylation of those and other esters of 6-aminopenicillanic acid (6-APA) with "any of the acyl groups found in the side chains of known antibacterial penicillins, especially the group of" the formula for D-(−)-2-phenylglycine which occurs in ampicillin.

U.S. Pat. No. 3,714,146 discloses, inter alia, cephalexin and the compound having the formula

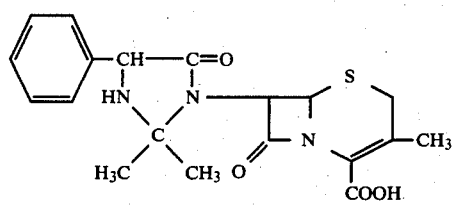

which is the acetone adduct of cephalexin and is also called hetacephalexin.

U.S. Pat. No. 3,489,752 discloses, inter alia, cefadroxil and the compound having the formula

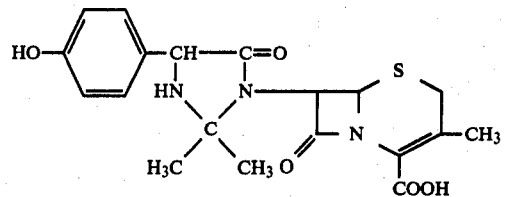

which is the acetone adduct of cefadroxil and is also called hetacefadroxil. The specification contains the very general statement, "Also included are the easily hydrolyzed esters or amides of such acids which may be converted to the free acid form by chemical or enzymatic hydrolysis," but no such esters are exemplified or named.

The methoxymethyl esters of each of the compounds having the structures set forth immediately above have been disclosed in U.S. Pat. No. 4,125,716.

The prior art contains numerous patents and publications directed to the preparation of deacetoxy cephalosporins (3-methyl-Δ³-cephems) by ring enlargement reactions of penicillin sulfoxides. Some of this art make general statements to the effect that substantially any known penicillin sidechain is suitable for use in the reaction. Alternatively, the art teaches that the resulting 3-methyl-Δ³-cephem compound may be cleaved to produce 7-ADCA and then reacylated with substantially any sidechain. During the ring enlargement reaction the carboxyl group of the penicillin sulfoxide must be protected to prevent decarboxylation. This is often done by utilizing an ester of the penicillin sulfoxide—the product being the corresponding 3-methyl-Δ³-cephem ester. Despite the voluminous prior art generated by numerous workers in this field, the instantly claimed compounds have not, to our knowledge, been described or disclosed in any of such prior art. The following are cited as more examples of broad disclosure patents in the ring enlargement field: Farmdoc 14260X; U.K. Pat. No. 1,430,944; U.S. Pat. Nos. 3,932,387 and 3,944,545.

In similar fashion there are many patents on new compounds or processes for making known compounds which contain broad disclosures with respect to β-lactam antibiotics and/or esters thereof. The following list presents a casual sample:

| | |
|---|---|
| Farmdoc 86586Y | U.K. 1,315,566 |
| Farmdoc 28688Y | U.K. 1,341,449 |
| Farmdoc 21182X | U.K. 1,421,526, |
| Farmdoc 14259X | U.K. 1,425,571 |
| Farmdoc 00144X | |
| Farmdoc 20401V | |
| Farmdoc 05417U | |
| Farmdoc 81607T | |
| U.S. Pat. No. 3,748,323 | |
| U.S. Pat. No. 3,885,233 | |
| U.S. Pat. No. 3,859,274 | |
| U.S. Pat. No. 3,862,004 | |
| U.S. Pat. No. 3,864,331 | |
| U.S. Pat. No. 3,873,519 | |
| U.S. Pat. No. 3,912,751 | |
| U.S. Pat. No. 3,931,405 | |
| U.S. Pat. No. 3,954,735 | |
| U.S. Pat. No. 4,012,518 | |

E. J. Corey et al., A New General Method for Protection of the Hydroxyl Function, Tetrahedron Letters, 11, 809–812 (1976) describe the preparation and use of methoxyethoxymethyl chloride (MEM chloride) to form ethers from alcohols.

β-Methoxyethoxymethyl chloride (MEM chloride) is advertised for sale by Aldrich Chemical Company, Inc., 940 West Saint Paul Avenue, Milwaukee, Wisconsin 53233, U.S.A. for the protection of alcohols by formation of the corresponding ether which can be subsequently cleaved easily and specifically by Lewis acids and especially anhydrous $ZnBr_2$ or $TiCl_4$ in $CH_2Cl_2$ solution at room temperature.

It was the object of the present invention to provide a derivative of orally absorbed cephalosporins and penicillins which would provide improved, that is, heightened or extended, blood levels or increased distribution into tissues upon oral administration compared to that of the parent antibiotic and, by comparison with the corresponding methoxymethyl esters, would exhibit greater stability to acids, would avoid the production of formaldehyde by metabolic breakdown and would avoid the use of carcinogenic reagents during their synthesis.

SUMMARY OF THE INVENTION

The objectives of the present invention have been achieved by the provision, according to the present invention, of an ester in which the group having the formula $-CH_2OCH_2CH_2OCH_3$ has replaced the hydrogen of the carboxyl group substituted on the bicyclic nucleus of a cephalosporin or a penicillin and particularly an ester in which the group having the formula $-CH_2OCH_2CH_2OCH_3$ has replaced the hydrogen of the carboxyl group substituted on the bicyclic nucleus of a cephalosporin or a penicillin and said cephalosporin or penicillin is selected from the group consisting of hetacephalexin, hetacefadroxil, hetacephaloglycin, oxacillin, cloxacillin, dicloxacillin, flucloxacillin, hetacillin, metampicillin, heta-amoxicillin and nafcillin.

There is further provided by the present invention an ester in which the group having the formula $-CH_2OCH_2CH_2OCH_3$ has replaced the hydrogen of the carboxyl group substituted on the bicyclic nucleus of a cephalosporin or a penicillin, said cephalosporin or penicillin containing a free primary amino group; or a nontoxic, pharmaceutically acceptable acid addition salt thereof and especially an ester in which the group having the formula $-CH_2OCH_2CH_2OCH_3$ has replaced the hydrogen of the carboxyl group substituted on the bicyclic nucleus of a cephalosporin or a penicillin, said cephalosporin or penicillin containing a free primary amino group and said cephalosporin or penicillin being selected from the group consisting of cephalexin, cephradine, cefadroxil, meta-chlorocefadroxil, meta-sulfonamidocephalexin, cefaclor, cefaparole, cefatrizine, cephaloglycin, ampicillin, epicillin, meta-chloroamoxicillin and amoxicillin; or a nontoxic, pharmaceutically acceptable acid addition salt thereof.

Preferred species of the present invention are the compounds having the formula

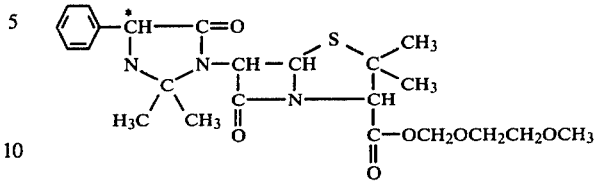

and the compound having the formula

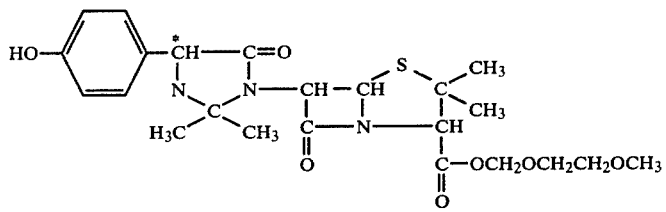

In their preferred form these compounds have the D-configuration at the carbon atom marked with an asterisk.

The nontoxic acid addition salts of those compounds of the present invention which contain a free primary amino group include mineral acid addition salts such as the hydrochloride, hydrobromide, hydroiodide, sulfate, sulfamate and phosphate and the organic acid addition salts such as the maleate, acetate, citrate, oxalate, succinate, benzoate, tartrate, fumarate, malate, mandelate, ascorbate and the like.

The compounds of this invention are useful in the treatment of bacterial infections in mammals, including man. They may be administered orally or parenterally but preferably are administered orally. When used orally, the compounds of this invention may be in capsule form, or as tablets, powders, liquid solutions, suspensions, elixirs, or the like. The compounds may be used alone or in combination with other active ingredients. They may be used in compositions including one or more pharmaceutically acceptable carriers as well as other ingredients such as stabilizers, binders, antioxidants, preservatives, lubricating agents, suspending agents, viscosity controlling agents, flavors and the like. Suitable compositions are well-known to those skilled in the penicillin and cephalosporin art.

The compounds of this invention may be administered over a broad dosage range, e.g. from about 5 to about 200 mg./kg. of body weight per day in divided doses. They are preferably administered over a dosage range of from about 5 to about 60 mg./kg. of body weight per day in divided doses. The most preferred adult dose is from 250 mg. to 500 mg. given every six hours.

There is also provided by the present invention the process for producing an ester of the present invention which comprises reacting a cephalosporin or penicillin, including hetacillin and heta-amoxicillin, in solution in a solvent which is preferably an anhydrous organic solvent such as methylene chloride and preferably in the form of a salt, as with a tertiary lower alkylamine such as triethylamine at room temperature or below, and preferably at about 0°–5° C., with about an equimolar amount of methoxyethoxymethyl chloride or methoxyethoxymethyl bromide or an equivalent alkylating derivative of methoxyethoxymethyl alcohol, and then recovering the desired product which is so provided.

In the alternative and when appropriate, a compound having a free primary amino group such as ampicillin is esterified in the same fashion and then converted to its acetone adduct by the procedures set forth in U.S. Pat. No. 3,198,804 to convert ampicillin to hetacillin.

In another alternative a nucleus such as 6-aminopenicillanic acid (6-APA) or 7-aminodesacetoxycephalosporanic acid (7-ADCA) is thus esterified and the resulting ester is acylated at the 6- or 7-amino group according to known procedures such as those set forth in U.S. Pat. Nos. 3,996,236; 2,985,648 and 3,140,282.

The following examples are given solely for purposes of illustration and not of limitation.

DESCRIPTION OF THE PREFERRED EMBODIMENTS

EXAMPLE 1

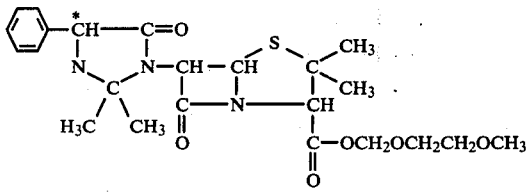

Methoxyethoxymethyl Ester of Hetacillin (RN-1492)

Ten grams of hetacillin were dissolved in 100 ml. dry methylene chloride by the addition of one equivalent of triethylamine (3.57 ml.) at 0°–5° C. To this solution there was then added 3.19 g. methoxyethoxymethyl chloride in 20 ml. of dry methylene chloride. Nitrogen was passed in during the reaction. The reaction mixture was stirred for three hours at 0°–5° C. and then allowed to stand overnight at 8° C. It was then washed three times with 50 ml. water. The organic phase was dried with $MgSO_4$ and the solvent was removed by distillation in vacuo to leave an oil which was then dissolved in 100 ml. acetone. After the addition of 100 ml. n-heptane the solution was held at 0°–8° C. overnight. The desired product, methoxyethoxymethyl ester of hetacillin, precipitated and was collected by filtration giving 8.8 g. (72% yield) with a second crop of 1.0 g. (8% yield).

Analytical data for the first crop were as follows:
IR—Consistent for structure.
NMR—Consistent: NMR indicates >95% purity with respect to acetone adduct group.

| Elemental Anal: | C | H | N | S | $H_2O$ |
|---|---|---|---|---|---|
| Theory: | 57.84 | 6.54 | 8.80 | 6.71 | 0 |

-continued

| Elemental Anal: | C | H | N | S | $H_2O$ |
|---|---|---|---|---|---|
| Found: | 57.27 | 6.50 | 8.71 | 6.78 | 0 |

TLC: (Acetone:Toluene 1:1) one spot.

EXAMPLE 2

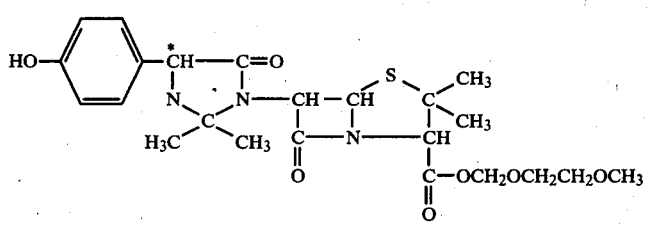

Methoxyethoxymethyl Ester of Heta-Amoxicillin (RN-1493)

The procedure of Example 1 was repeated with the substitution for the hetacillin therein of an equimolar weight of heta-amoxicillin (also called p-hydroxyhetacillin or the acetone adduct of amoxicillin) to produce the title compound. The product appeared by NMR to be 85–90% pure with respect to the acetone adduct group.

Cold storage of all these compounds at less than 10° C. is recommended.

BIOLOGICAL TESTING

Bacteria. The organisms, preponderantly of recent clinical origin, were obtained from numerous sources of broad geographical distribution. Obligate anaerobes were maintained in Egg Meat Medium (Difco); Mycobacterium was stored on Lowenstein Medium (Jensen Modification; Difco). The techniques of storing all other organisms have been described previously [Leitner et al., BL-S640, A Cephalosporin with a Broad Spectrum of Antibacterial Activity: Properties in vitro, Antimicrob. Agents Chemother., 7, 298–305 (1975)].

Antibiotic spectrum. The growth-inhibitory activity of the compounds was determined by the antibiotic dilution technique. Procedures were as follows:

Aerobic organisms (excluding Mycobacterium). Except for Haemophilus and Neisseria, the assay was performed in Mueller-Hinton Medium (Difco). For fastidious organisms, i.e., Streptococcus, Listeria, Pasteurella, Bordetella and Vibrio, the medium was supplemented with 4% defibrinated sheep blood. The antibiotic susceptibility of Haemophilus and Neisseria was determined in GC Medium Base (BBL) supplemented with 1% Hemoglobin (BBL) and 1% Isovitalex (BBL).

Overnight broth cultures of an exponentially growing culture (Neisseria) served as the source of inoculum. A volume of approximately 0.003 ml. of the undiluted or diluted culture was applied to the surface of the antibiotic-containing agar plates with the inoculator of Steers et al., An Inocula Replicating Apparatus for Routine Testing of Bacterial Susceptibility to Antibiotics, Antibiot. Chemother., 9, 307–311, (1959). Cultures of Neisseria, *Streptococcus pneumoniae, S. viridans* and *S. pyogenes* were used without dilution; those of all other organisms were diluted 100-fold. The inoculum contained about $10^3$ viable cells for Neisseria, $10^5$ for *S. pneumoniae* and *S. pyogenes*, $10^6$ for *S. viridans* and $10^4$ for all other species. The culture plates were incubated at 37° C. either overnight or for 24 hours (Haemophilus) and the minimum inhibitory concentration (MIC), i.e., the lowest concentration of antibiotic which prevents visible growth, was recorded.

Antibiotic Concentration in Blood. Male Swiss-Webster mice, weighing 19–22 g. were given 0.2 ml. of antibiotic solutions at appropriate concentrations by intramuscular injection. The vehicle was 0.01% phosphate buffer at pH 7.0. Eight animals were used for each dose level (5, 10, 20 and 40 mg./kg.). Blood samples (0.03 ml.) were obtained from the orbital sinuses by means of heparinized capillary tubes (Clay Adams) at 0.25, 0.5, 1 and 1.5 hours after administration of the compound. Paper discs, 6.35 mm. in diameter, were impregnated with the blood and the antibiotic activity assayed by the diffusion technique using Seed Agar (BBL) inoculated with *Bacillus subtilis* ATCC 6633. A standard line relating the diameter of the inhibition zone to drug concentration was obtained by assaying the compounds at known concentrations in heparinized mouse blood.

Treatment of Systemically Infected Mice. The procedures were identical with those published previously [Leitner et al., BL-S640, A Cephalosporin With a Broad Spectrum of Antibacterial Activity; Bioavailability and Therapeutic Properties in Rodents, Antimicrob. Agents Chemother., 7, 306–310, (1975)], except that the hog gastric mucin used in infections with *Staphylococcus aureus* No. 2 was purchased from American Laboratories, Inc., Omaha, Nebraska (Lot No. 154163) and that the medium used to suspend all other organisms contained 3% (rather than 4%) hog gastric mucin (type 1701W, Wilson Laboratories, Inc., Park Forest South, Ill.

TABLE 1

In Vitro Activity

| Organism | MIC (mcg./ml.) RN-1492 Hetacillin MEM Ester | Hetacillin | Ampicillin |
|---|---|---|---|
| Str. pneumoniae | 0.004 | 0.004 | 0.004 |
| Str. pyogenes | 0.008 | 0.004 | 0.008 |
| S. aureus | 0.06 | 0.008 | 0.03 |
| S. aureus + 50% serum | 0.13 | 0.016 | 0.06 |
| S. aureus Pen-Res. | >125 | 125 | 125 |
| S. aureus Meth-Res. | 63 | 16 | 16 |
| Str. faecalis | 0.5 | 0.13 | 0.13 |
| E. Coli | 2 | 1 | 1 |
| E. Coli | 63 | 32 | 63 |
| K. pneumoniae | 63 | 63 | 63 |
| K. pneumoniae | 32 | 63 | 32 |
| Pr. mirabilis | 0.25 | 0.03 | 0.06 |
| Pr. vulgaris | 0.25 | 0.06 | 0.13 |
| Pr. morganni | 32 | 16 | 125 |
| Pr. rettgeri | 16 | 8 | 8 |
| Ser. marcescens | 32 | 16 | 16 |
| Ent. cloacae | 63 | 32 | 32 |
| Ent. cloacae | 63 | 63 | 32 |
| Ps. aeruginosa | 63 | 63 | 63 |
| Ps. aeruginosa | 125 | 125 | >125 |

TABLE 2

In Vitro Activity

| Organism | MIC (mcg/ml.) RN-1493 Hetamoxicillin MEM Ester | Amoxicillin |
|---|---|---|
| Str. pneumoniae | 0.004 | 0.004 |
| Str. pyogenes | 0.008 | 0.004 |
| S. aureus | 0.06 | 0.03 |
| S. aureus + 50% serum | 0.25 | 0.06 |
| S. aureus Pen-Res. | 125 | >125 |
| S. aureus Meth-Res. | 63 | 32 |
| Str. faecalis | 0.5 | 0.06 |
| E. coli | 2 | 0.5 |
| E. coli | 63 | >125 |
| K. pneumoniae | 63 | 125 |
| K. pneumoniae | 63 | >125 |
| Pr. mirabilis | 0.5 | 0.06 |
| Pr. vulgaris | 0.5 | 0.06 |
| Pr. morganii | 16 | 125 |
| Pr. rettgeri | 32 | 16 |
| Ser. marcescens | 32 | 32 |
| Ent. cloacae | 63 | 63 |
| Ent. cloacae | 63 | 125 |
| Ps. aeruginosa | 63 | 125 |
| Ps. aeruginosa | 63 | >125 |

TABLE 3

Mouse Blood Levels of the Methoxyethoxymethyl Esters of Hetacillin (RN-1492) and Hetamoxicillin (RN-1493) After Oral Administration of 100 mg./kg. Body Weight.

| Minutes After Administration | Blood Levels (mcg./ml.)* | | | |
|---|---|---|---|---|
| | RN-1492 Hetacillin MEM Ester | Ampicillin | RN-1493 (Hetamoxicillin MEM Ester | Amoxicillin |
| 15 | 25.2 | 3.5 | 7.2 | 9.5*** |
| 30 | 12.7 | 6.6 | 6.6 | 16.9 |
| 60 | 4.7 | 6.8 | 3.1 | 14.2 |
| 90 | 2.4 | 4.3 | 2.2 | 8.7 |
| 120 | 1.2 | 2.5 | 1.6 | 6.3 |
| 180 | 0.5 | 1.1 | 1.1 | 3.1 |

*Blood level values represent average of two experiments
Assay Organism: *Bacillus subtilis* ATCC 6653
**Reported as mcg./ml. of ampicillin
***Reported as mcg./ml. of amoxicillin

TABLE 4

In Vitro Activity of RN-1492, the Methoxyethoxymethyl (MEM) Ester of Hectacillin

| Organism | No. of Strains | MIC (mcg./ml.)* RN-1492 | Ampicillin |
|---|---|---|---|
| S. aureus (lacking penase) | 6 | 0.18 | 0.07 |
| S. faecalis | 6 | 2 | 1 |
| S. pneumoniae | 7 | 0.032 | 0.02 |
| S. pyogenes | 6 | 0.027 | 0.016 |
| S. viridans | 3 | 0.05 | 0.05 |
| S. viridans | 1 | 0.25 | 0.063 |
| s. viridans | 1 | 0.5 | 0.35 |
| Streptococcus sp. (β-hemolytic) | 6 | 0.13 | 0.063 |
| E. coli | 1 | 2 | 0.5 |
| E. coli | 3 | 5 | 2.5 |
| E. coli | 1 | 63 | 63 |
| E. coli | 1 | >125 | >125 |
| K. pneumoniae | 1 | 63 | 32 |
| K. pneumoniae | 1 | >125 | >125 |
| E. cloacae | 2 | >125 | 63 |
| P. mirabilis | 4 | 4 | 2 |
| P. mirabilis | 2 | >125 | >125 |
| P. rettgeri | 1 | 0.25 | 0.13 |
| P. rettgeri | 1 | 16 | 4 |
| P. retgeri | 2 | 63 | 32 |
| p. vulgaris | 2 | 0.5 | 0.35 |
| S. marcescens | 1 | >125 | 63 |
| S. marcescens | 1 | >125 | >125 |

*Geometric mean MIC value where applicable

TABLE 5

Efficacy of RN-1492 (Methoxyethoxymethyl Ester of Hetacillin) Following Oral Treatment of Mice Systemically Infected with Various Organisms.

| Organism | Challenge (No. of Organisms) | PD$_{50}$/Treatment (mcg./ml.)* | |
|---|---|---|---|
| | | RN-1492 | Ampicillin |
| S. aureus | $1 \times 10^5$ | 0.08 | 0.08 |
| S. aureus | $1.3 \times 10^5$ | 0.06 | 0.08 |
| E. coli | $7.2 \times 10^5$ | 43 | 14 |
| E. coli | $1.2 \times 10^6$ | 33 | 33 |
| P. mirabilis | $1.5 \times 10^7$ | 150 | 114 |
| P. mirabilis | $1.9 \times 10^7$ | 50 | 50 |

*Treatment Schedule:
S. aureus and E. coli were treated at 1 and 3.5 hours/post-challenge; P. mirabilis was treated at 0 and 2 hours post-challenge.

EXAMPLE 3

A. Methoxyethoxymethyl Ester of Hetacillin (RN-1492)

To 20 g. (0.0513 m.) of hetacillin (mw=390 g./mole) in 200 ml. of dry $CH_2Cl_2$ was added 7.65 ml. (5.55 g., 0.055 mole) of triethylamine (TEA) (mw=101.19 g./mole), 7% excess, slowly at 0°–5° C. The solution was purged with $N_2$ throughout the reaction. Methoxyethoxymethyl chloride (MEM chloride), 6.39 g. (0.0513 mole) mw=124.5 g./mole, in 25 ml. of dry $CH_2Cl_2$ was then added dropwise in about 10 minutes and stirred at −5° C. for 1.5 hours. The reaction mixture was poured into 150 ml. of water (cooled to about −5° C.), separated and the wash of the $CH_2Cl_2$ layer with another 150 ml. of water was repeated. The $CH_2Cl_2$ solution was dried with $MgSO_4$ (anhydrous). Stripped (removed the $CH_2Cl_2$ by distillation in vacuo) to obtain the product as a gummy solid. Added 100 ml. diethyl ether (EtOEt) to the solid and stirred. After collecting by filtration and washing with EtOEt 17.33 g. of methoxyethoxymethyl ester of hetacillin was obtained as mostly crystalline white solid. This is a 71% yield.

12 g. of the above solid was dissolved in 14 ml. of acetone to which 140 ml. of EtOEt was then added slowly. To the resulting clear solution was added heptane (50 ml.) slowly. The resulting cloudy solution was seeded and left in a cold room (about 8° C.) overnight and then chilled to −10° C. for 1 hour. The resulting precipitate was then collected by filtration and washed with 50 ml. of 1:1=EtOEt:heptane to yield 10 g. methoxyethoxymethyl ester of hetacillin (recovery of 83.3%) as a snow-white crystalline solid.

| Elemental Anal.: | C | H | N | S | H$_2$O |
|---|---|---|---|---|---|
| Calculated: | 57.84 | 6.54 | 8.80 | 6.7 | 0 |
| Found: | 57.88 | 6.32 | 8.88 | 6.56 | 0 |

TLC: (Toluene:Acetone=1:1): one zone

EXAMPLE 4

B. Methoxyethoxymethyl Ester of Heta-Amoxicillin (RN-1493)

To 20 g. (0.0493 mole) of p-hydroxyhetacillin (mw=406.0 g./mole) in 200 ml. of $CH_2Cl_2$ was added 9.8 ml. (0.0703 mole, 44% excess) of TEA (mw=101.19 g/mole) dropwise at 0°–5° C. A complete solution was obtained after about 5 minutes with stirring. 7.7 g. (0.0618 mole, 25% excess) of MEM chloride (mw=124.5 g./mole) in 20 ml. of $CH_2Cl_2$ was added to the above solution in about 5 minutes. The mixture was stirred for 1 hour then left in a cold room (about 8° C.) for 16 hours. The reaction mixture was then poured into 200 ml. of cold water (about 0° C.) and was stirred vigorously for 10 minutes (pH=9.0). This operation was repeated once more after separation of the organic layer. The aqueous layers were then extracted once with 50 ml. of $CH_2Cl_2$. The $CH_2Cl_2$ solutions were combined, dried over $MgSO_4$, stripped to a volume of about 60 ml. and polish filtered. To the filtrate there was added 20 ml. of acetone, then 100 ml. of EtOEt slowly. Crystallization of methoxyethoxymethyl ester of heta-amoxicillin occurred. The slurry was stirred at room temperature for one hour. The product was collected by filtration to give 12.3 g. as a snow-white crystalline solid (51% yield).

50 ml. of heptane was added to the filtrate and the mixture was left in a cold room overnight and then filtered to provide 2.8 g. of a second crop of product as a snow-white crystalline solid (11.5% yield). Total=51% plus 11.5%=62.5%.

12 g. of the first crop was stirred with 200 ml. of acetone for 3 hours. The insoluble fraction (10 g.) again stirred with 100 ml. of water at 0° C. for 2 hours. 9.8 of purified methoxyethoxymethyl ester of heta-amoxicillin was thus obtained. Recovery yield=82%.

| Elemental Anal.: | C | H | N | S | H$_2$O |
|---|---|---|---|---|---|
| Calculated: | 55.97 | 6.33 | 8.5 | 6.5 | 0 |
| Found: | 55.21 | 6.40 | 8.33 | 6.41 | 0 |
| Repeat: | 55.31 | 6.33 | 8.45 | — | — |

TLC: (Toluene:Acetone=1:1): one zone

This invention is capable of industrial application.

We claim:

1. An ester in which the group having the formula —$CH_2OCH_2CH_2OCH_3$ has replaced the hydrogen of the carboxyl group substituted on the bicyclic nucleus of a penicillin and said penicillin is selected from the group consisting of oxacillin, cloxacillin, dicloxacillin, flucloxacillin, hetacillin, metampicillin, heta-amoxicillin and nafcillin.

2. An ester in which the group having the formula —$CH_2OCH_2CH_2OCH_3$ has replaced the hydrogen of the carboxyl group substituted on the bicyclic nucleus of a penicillin, said penicillin containing a free primary amino group and said penicillin being selected from the group consisting of ampicillin, epicillin, metachloroamoxicillin and amoxicillin; or a nontoxic, pharmaceutically acceptable acid addition salt thereof.

3. The compound having the formula

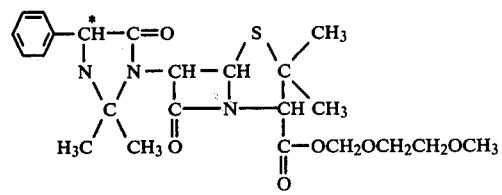

having the D-configuration at the carbon atom marked with an asterisk.

4. The compound having the formula

11
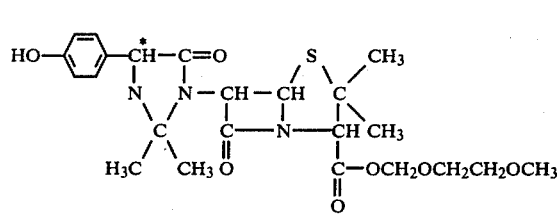
having the D-configuration at the carbon atom marked with an asterisk.
* * * * *
12
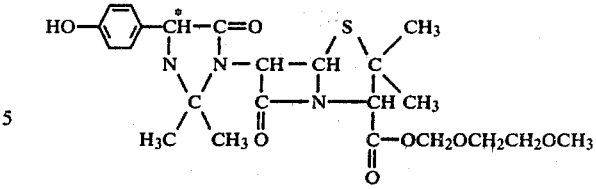
having the D-configuration at the carbon atom marked with an asterisk.
* * * * *